United States Patent [19]

Klemm

[11] Patent Number: Plant 6,996

[45] Date of Patent: Aug. 22, 1989

[54] GERANIUM PLANT NAMED MANEPI

[75] Inventor: Siegfried Klemm, Stuttgart, Fed. Rep. of Germany

[73] Assignee: Klemm & Sohn, Stuttgart, Fed. Rep. of Germany

[21] Appl. No.: 237,404

[22] Filed: Aug. 29, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new geranium cultivar particularly distinguished by the very large size of the individual florets, of which about sixty-five comprise the umbel-formed flower cluster which is distinctive of cultivated geranium varieties. The individual florets are further distinguished by their deep red coloration and the number of imbricated petals which form large, rather flat, solid red florets of about 5 cm. in diameter.

1 Drawing Sheet

BACKGROUND OF THE NEW PLANT

My new geranium variety originated as a seedling of a hybrid resulting from my crossing of the variety 'Palais' with the variety 'Bruni' as the pollen parent, both being unpatented varieties, at my nursery at Stuttgart, West Germany, in 1985, this new plant having been selected from a group of seedlings of the said hybrid. The selection of this particular seedling was made because of the large size of the individual florets and their grouping to form large clusters of a brilliant red color. The selected plant was asexually reproduced by me and under my direction, by means of cuttings, through several successive generations at Stuttgart, which demonstrated that the distinguishing charcteristics of this new plant would hold true from generation to generation and appeared to be firmly fixed. Propagation of this new plant is now being carried on by means of cuttings at my nursery at Stuttgart.

DESCRIPTION OF THE DRAWING

My new geranium cultivar is illustrated by the accompanying photographic drawing, which illustrates the form and color of the individual florets, as well as buds in several stages of opening and an umbel-formed group of buds for forming a full cluster, the color rendition being as nearly true to that herein specified as is reasonably possible to obtain by conventional photographic procedures.

DESCRIPTION OF THE NEW PLANT

The following is a detailed description of my new variety of geranium plant as observed at Stuttgart in 1988, with color designations according to The R.H.S. Colour Chart published by The Royal Horticultural Society of London, England.

THE PLANT

Origin: Seedling.
Parentage:
- *Seed parent.*—The variety 'Palais' (unpatented).
- *Pollen parent.*—The variety 'Bruni' (unpatented).

Classification:
- *Botanic.*—*Pelargonium zonale* hybrid.
- *Commercial.*—Geranium.

Form: Bush.
Shape: Spreading.

Height: Averaging about 30 cm.
Growth: Bushy and upright at a medium growth rate and spreading to a width of about the same as the plant height.
Branching: Normal.
Main stem length: About 10 to 12 cm.
Foliage:
- *Quantity.*—Abundant.
- *Size of leaf.*—About 8.5 cm. long and about 7 cm. wide.
- *Leaf shape.*—Kidney shaped with bicrenate margin.
- *Height above soil.*—About 12 cm.
- *Texture.*—Smooth.
- *Ribs and veins.*—Five main veins on each leaf.
- *Color.*—Upper side — Medium Green. Under side — Lighter Green.

THE BUD

Size: Normal.
- *Diameter.*—About 12 mm.
- *Length.*—About 12 to 15 mm.

Shape: Elliptic with pointed apex.
Rate of opening: Medium.
Color of petals:
- *When sepals first divide.*—Very light pink.
- *When petals begin to unfurl.*—Pink to red.

Sepals:
- *Number.*—Five.
- *Shape.*—Elliptical
- *Character.*—The sepals stand up when the flowers open.
- *Color.*—Green.

Peduncle:
- *Length.*—About 16 cm.
- *Character.*—Rigid.
- *Color.*—Medium green.

INFLORESCENCE

Blooming habit: Continuous and profusely from early Spring through midseason to Fall.
Florets:
- *Size.*—Large. Diameter — About 5 cm. Depth — About 1 cm.
- *Borne.*—Singly on a stem of an umbel-formed cluster.

*Shape.*—When bloom first opens, cup-shaped. When bloom matures, flat cup.

Petalage:

*Number of petals.*—6 to 9.

*Arrangement.*—Imbricated.

*Form.*—Broad with round apex and entire margins.

*Texture.*—Soft

*Aspect.*—Satiny

*Color.*—RHS 40-A with a dark "eye".

*Petaloids.*—Number: 1 or 2. Size. About 4 to 7 mm. Color: Red.

Peduncle:

*Length.*—About 16 cm.

*Color.*—Green

*Character.*—Strong and upright.

Persistence: The petals stay on the stem about thirteen to fourteen days.

Fragrance: None

Disease resistance: Good resistance against Botrytis as observed in the region of Stuttgart, West Germany.

REPRODUCTIVE ORGANS

Stamens:

*Number.*—Seven.

*Arrangement.*—In a ring around the pistil.

*Anthers.*—Size: About 1.5 cm. Color: Orange.

*Filaments.*—Length: About 4 mm. Color: White.

*Pollen.*—Color: Orange.

Pistil:

*Number.*—One.

*Style.*—Length: About 5 mm. Color: White-green.

*Stigma.*—Five cells. Color: Pink frosted glas.

Character of ovaries: Normal.

THE FRUIT

Fertility: The fruit is fertile.

Shape: Ovoid

Color at maturity: Dark brown.

A very well growing and new red geranium variety providing a very well shaped bush with dense clusters of about seven to ten bright red florets, each of which has a dark 'eye' providing a very expressive appearance.

I claim:

1. The new and distinctive geranium cultivar, substantially as herein shown and described, distinguished by the very large size of its red florets, closely grouped to provide brilliant umbel-formed clusters.

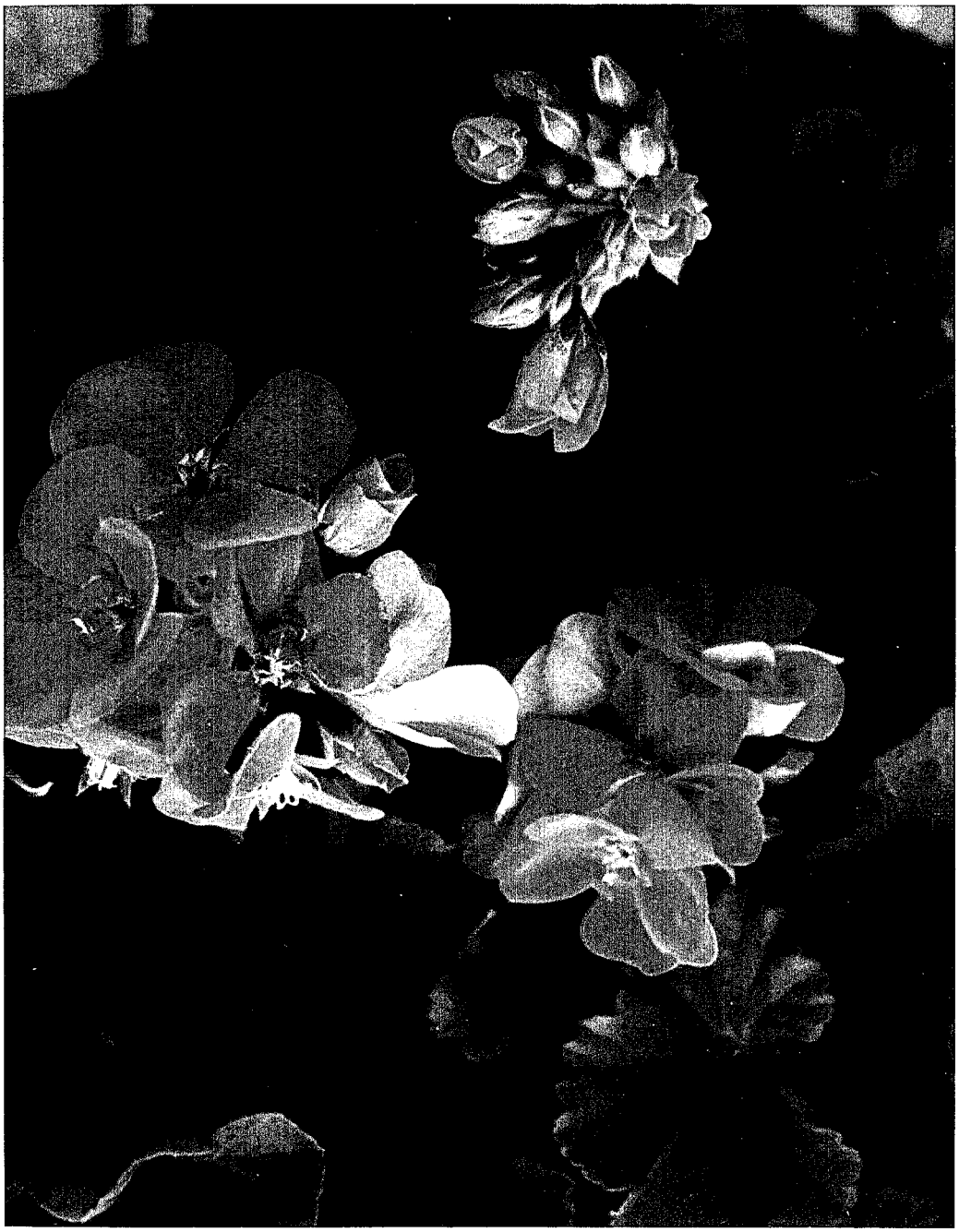

* * * * *